Figure 1:
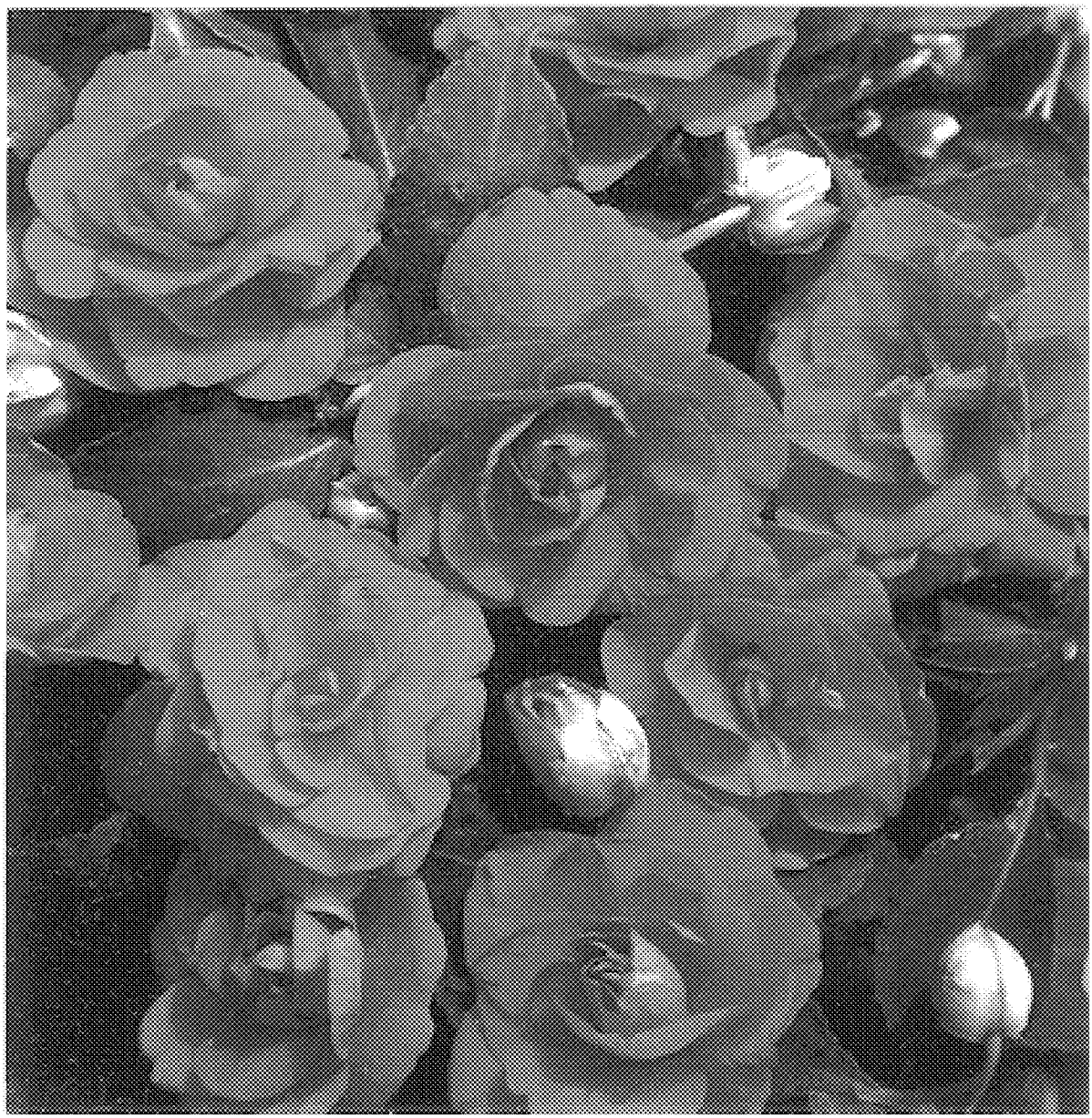

US00PP11404P

United States Patent [19]

Jonkers

[11] Patent Number: Plant 11,404

[45] Date of Patent: Jun. 6, 2000

[54] IMPATIENS PLANT NAMED 'DIDI RED'

[75] Inventor: J. B. (Hanneke) Jonkers, RK Hoorn, Netherlands

[73] Assignee: Goldsmith Plants, Inc., Gilroy, Calif.

[21] Appl. No.: 09/078,642

[22] Filed: May 14, 1998

[51] Int. Cl.[7] ..... A01H 5/00

[52] U.S. Cl. ..... Plt./317

[58] Field of Search ..... Plt./317

[56] References Cited

PUBLICATIONS

GTITM UPOVROM Citation for 'Didi Red' As per QZ PBR 952883; Oct. 25, 1995.

*Primary Examiner*—Howard J. Locker
*Assistant Examiner*—Kent L. Bell
*Attorney, Agent, or Firm*—Rothwell, Figg, Ernst & Kurz

[57] ABSTRACT

A new and distinct cultivar of Impatiens plant, and named 'Didi Red' is provided. 'Didi Red' is distinct in its red colored fully double flowers, its early and free flowering, and its basal branched, compact growth habit.

1 Drawing Sheet

BACKGROUND OF THE NEW PLANT

The present invention comprises a new and distinct cultivar of impatiens, botanically known as *Impatiens walleriana*, and hereinafter referred to by the cultivar name 'Didi Red', and is characterized by the following combinations of repeatedly observed traits:

1. Fully double flowers,
2. early flowering,
3. compact basal branching, and
4. free flowering.

Asexual reproduction of this cultivar by stem cuttings taken during November, 1996, at Andijk, The Netherlands, has demonstrated that the characteristics of the new cultivar as herein described are firmly fixed and are retained through successive generations of such asexual propagation, such reproduction establishing that the plant does in fact maintain the characteristics described in successive generations. The female parent (i.e., the seed parent) was an *Impatiens walleriana* named IN-1 791-12 (unpatented) and the male parent (i.e., pollen parent) was an *Impatiens walleriana* named IM-795-3 (unpatented). The cross was made in 1995 and the seedling was selected in 1996.

This new cultivar has been identified as Impatiens 'Didi Red'. It is possible that other identification will be adopted in the trade, but the name selected will serve for the purposes hereof.

DESCRIPTION OF THE PHOTOGRAPH

This new impatiens plant is illustrated by the accompanying photographic drawing which shows blooms, buds, and foliage of the plant in full color, the colors shown being as true as can be reasonably obtained by conventional photographic procedures.

FIG. 1 shows buds, blooms and foliage of the new plant

DESCRIPTION OF THE NEW CULTIVAR

The following observations and measurements describe plants grown outside in the field in Andijk, The Netherlands. Measurements were recorded in August, 1997, on plants approximately 14 weeks old. Fully developed organs were used for measurements and color descriptions, unless otherwise indicated. Color references are made to the R.H.S.

Colour Chart of The Royal Horticultural Society, London, England, except where general color terms of ordinary significance are used. 'Didi Red 'has not been observed under all possible environmental conditions. The phenotype may vary with variations in environment and horticultural practices, such as temperature, light intensity, day length, fertilization and propagation procedure, without any change in genotype.

Parentage

*Female parent.*—*Imipatiens walleriana* IN-1 791-12 (unpatented).

*Male parent.*—*Impatiens walleriana* IM-795-3 (unpatented).

Propagation:

*Type cutting.*—Stem (internodal) cutting with two nodes and attached leaves.

*Time to initiate roots.*—10–14 days at 70–75 degrees F. with a fully developed root mass at 21 days.

*Rooting habit.*—Fibrous, branching, adventitious root system.

Plant Descriptions:

*Form.*—Upright.

*Growth habi.*—Upright branching plant habit with upper leaves and flowers produced in whorls. When grown in a 4 inch pot for 10–12 weeks the height is approximatley 4–5 inches and the width is approximately 5 inches.

*Foilage description.*—Leaves are simple. Lower leaf arrangement is alternate with upper leaves arranged in whorls of 5. Leaf shape is lanceolate to elliptic with acute apex and acute base. Leaf size is 4.5 cm×3 cm. Leaf margin is crenate with ciliation. Leaf surface is glabrous. Leaf color is green. The upper surface is yellow-green group 147A. Under surface is yellow-green group 147B with purple mottling 182B. Venation is pinnate.

*Petiole.*—Petiole length is 2 cm; and diameter is 0.2 cm; Color is yellow-green 147C.

Flower description:

*Flowering habit.*—Rooted cutting to full flowering plant in seven weeks. Indeterminate, flowering continuously. Flowers develop in the upper leaf axils.

*Natural flowering season.*—Flowers continuously throughout the year.

*Flowers borne.*—On pedicels which are yellow-green 145A and 3 cm long in clusters of 2–7 flowers with a peduncle color of yellow-green 145A and length of 2 cm long.

*Spur.*—Short spurred; length is 3.5 cm; color is 145C.

*Buds.*—Buds are oval-shaped at first color 51A and 145D; size is 1.5 cm×1.1 cm.

*Quantity of flowers.*—Floriferous. Each axillary cluster of 2–7 flowers developing progressively from the leaf whorls so that buds as well as mature flowers are visible at the same time in large numbers.

*Petals.*—Number of petals 20–30, with all petals overlapping. Outer petals average 1.7 cm length×1.5 cm width and inner petals average 1.0 cm length×0.5 cm width. All petals are slightly cupped.

*Flower color.*—Upper surface: Red group 53C. Lower surface: Red group 53D.

*Flower size.*—Approximately 4 cm wide and 4 cm long.

*Reproductive organs.*—No reproductive organs.

DISEASE AND INSECT RESISTANCE

No known susceptibility to diseases or insects noted to date.

COMPARISON WITH THE KNOWN CULTIVARS

When 'Didi Red' is compared to Impatiens 'Fiesta Salsa Red' (unpatented), it is found that 'Didi Red' exhibits a more vigorous plant habit and is also more floriferous.

When 'Didi Red' is compared to 'IN-1791-12' and 'IM-795-3', the parental cultivars, the instant cultivar has double flowers and the parental cultivars are both single flowering.

When 'Didi Red' is compared to co-pending U.S. Plant Pat. application Ser. No. 09/078,644 for Impatiens 'Didi Scarlet', the primary difference is the color. 'Didi Red' has flowers colors of R.H.S. 53C and 53D and 'Didi Scarlet' has flower colors of R.H.S. 45C and 45D.

I claim:

1. A new and distinct cultivar of Impatiens plant named 'Didi Red', substantially as described and illustrated herein, characterized particularly as to novelty by its fully double red flowers, its early and free flowering, and its basal branched, compact growth habit.

* * * * *